US008444543B2

(12) United States Patent
Fenster et al.

(10) Patent No.: US 8,444,543 B2
(45) Date of Patent: May 21, 2013

(54) APPARATUS AND COMPUTING DEVICE FOR PERFORMING BRACHYTHERAPY AND METHODS OF IMAGING USING THE SAME

(75) Inventors: Aaron Fenster, London (CA); Lori Gardi, London (CA); Donal Downey, London (CA); Chandima Edirisinghe, London (CA); Mingyue Ding, London (CA)

(73) Assignee: Robarts Research Institute, London, Ontario (CA)

( * ) Notice: Subject to any disclaimer, the term of this patent is extended or adjusted under 35 U.S.C. 154(b) by 1023 days.

(21) Appl. No.: 12/206,180

(22) Filed: Sep. 8, 2008

(65) Prior Publication Data

US 2009/0198094 A1     Aug. 6, 2009

Related U.S. Application Data

(63) Continuation of application No. 11/970,422, filed on Jan. 7, 2008, now abandoned, which is a continuation of application No. 10/592,051, filed as application No. PCT/CA2005/000355 on Mar. 9, 2005, now abandoned.

(60) Provisional application No. 60/647,420, filed on Jan. 28, 2005, provisional application No. 60/551,006, filed on Mar. 9, 2004.

(51) Int. Cl.
*A61N 5/00* (2006.01)
(52) U.S. Cl.
USPC ............................................................ 600/3
(58) Field of Classification Search
USPC ....................................................... 600/1–8
See application file for complete search history.

(56) References Cited

U.S. PATENT DOCUMENTS 5,078,140 A   1/1992 Kwoh
6,505,065 B1   1/2003 Yanof et al.

FOREIGN PATENT DOCUMENTS

EP         1088524    *  4/2001

* cited by examiner

*Primary Examiner* — John Lacyk
(74) *Attorney, Agent, or Firm* — Marsh Fischmann & Breyfogle LLP

(57) ABSTRACT

An apparatus for determining a distribution of a selected therapy in a target volume is provided. A three-dimensional ultrasound transducer captures volume data from the target volume. A computing device is in communication with the three-dimensional ultrasound transducer for receiving the volume data and determining the distribution of the selected therapy in the target volume along a set of planned needle trajectories using the volume data. At least one of the needle trajectories is oblique to at least one other of the planned needle trajectories.

14 Claims, 17 Drawing Sheets

APPARATUS AND COMPUTING DEVICE FOR PERFORMING BRACHYTHERAPY AND METHODS OF IMAGING USING THE SAME

CROSS-REFERENCE TO RELATED APPLICATIONS

This application is a Continuation of U.S. patent application Ser. No. 11/970,422 filed Jan. 7, 2008, which is a Continuation of U.S. patent application Ser. No. 10/592,051 filed Mar. 9, 2005, which is a U.S. National Application based on International Application No. PCT/CA2005/000355 filed Mar. 9, 2005, which is based on U.S. Provisional Patent Application Ser. No. 60/551,006 filed Mar. 9, 2004 and U.S. Provisional Patent Application Ser. No. 60/647,420 filed Jan. 28, 2005, the disclosures of which are hereby explicitly incorporated by reference herein.

FIELD OF THE INVENTION

The present invention relates generally to imaging systems and, specifically, to an apparatus and computing device for performing brachytherapy and methods of imaging using the same.

BACKGROUND OF THE INVENTION

Ultrasound-guided interventional procedures such as breast biopsies and prostate brachytherapy are well-known. Needles can be inserted into the body and either obtain a biopsy sample or deliver a dose of a selected therapy. For biopsies, it is desirable to target a specific volume when obtaining a tissue sample. Where a dose is being administered to a target volume, it is desirable to track the precise location of the needle delivering the dose in real-time to ensure that the therapy is delivered according to plan.

Radioactive seeds can be used as a therapy to treat tumors in prostates. In order to ensure adequate coverage of the therapy, it is desirable to implant the seeds a pre-determined distance apart. If the distance between the seeds is too large, tissue between the seeds may not receive the amount of therapy needed for the treatment. If, instead, the seeds are too closely positioned, the tissue can be over-exposed. In conventional brachytherapy, a template having a plurality of holes for guiding needle placement is used. The needle trajectories obtained using these holes are parallel. Where the target volume is of an irregular shape or is blocked by another anatomical feature, the use of such parallel trajectories can provide results that are less than desirable, especially where there is interference from the pubic arch. One of the results of such issues are "cold spots", or areas with less-than-desired therapy. More recent templates have been suggested that provide for oblique trajectories, but the trajectories are fixed and may not provide results that are desirable in many cases.

The use of robots has been suggested to provide oblique trajectories in brachytherapy. The methods proposed, however, provide less-than-desired results in some circumstances. For example, the systems disclosed by U.S. Pat. No. 6,505,065 to Yanof et al. and by "Robotically Assisted Prostate Brachytherapy with Transrectal Ultrasound Guidance—Preliminary Experiments", by Fichtinger et al. require that a physician manually position a robotic assembly that inserts a brachytherapy needle. The manual positioning of the robotic assembly is labor-intensive and slow, and is prone to human error.

Factors such as prostate motion, bleeding and swelling during implantation, TRUS imaging artefacts, migration of the seeds in the needle tracks, and needle deflection contribute to errors between the preplan and the actual prostate dose distribution. Thus, verification of the actual locations of the seeds relative to the prostate margin, rectal wall and bladder is needed intra-operatively to allow adjustments to the plan to correct for potential "cold spots" (dynamic re-planning). Intra-procedural re-planning reduces the probability that one or more additional brachytherapy procedures need to be performed by monitoring the implanted dose and adjusting the dosimetry accordingly. Such follow-up procedures are complex in that the patient must be placed in the same position as for the original procedure, there may have been shifting, swelling or changes in the shape of the prostate since the original procedure.

Re-planning the dosimetry of the brachytherapy is currently difficult when performed using CT, in which case the re-planning can typically be performed only once due to the radiation concerns and the time associated with the CT procedure. If, instead, ultrasound imaging is used, the image data is generally insufficient to permit an accurate re-plan even with the advent of "echoseeds".

Seed segmentation in US images is extremely difficult primarily for 4 reasons: (i) calcifications and other echogenic structures can mimic the bright seed appearance, making seed identification difficult, (unlike the situation in a CT); (ii) there are many seeds—typically 80-100 are implanted; (iii) the seed brightness in the US image varies, depending on its orientation relative to the transducer (much brighter when oriented parallel due to specular reflection); and (iv) the small bright appearance of the seeds are superimposed on a highly cluttered background.

Seed segmentation is an active investigation area in medical image analysis. Most of the reports were concentrated on localization of the seeds in CT or fluoroscopic images. One approach to solve this problem involved the use of multiple projections of fluoroscopic images as a means to reconstruct the 3D positions of the seeds. Since the projection of the seeds overlapped in the images, complicated seed image matching algorithms were required. Another approach is to use 3D CT images. Due to the spacing between CT slices, typically 1 to 5 mm, the same seed may appear in different slices, requiring correction.

Compared to seed segmentation in fluoroscopic or CT images, the challenges of seed segmentation in 3D transrectal ultrasound (TRUS) images are: 1) low contrast-to-signal ratio due to speckle in 3D TRUS images; 2) image brightness of a seed depends on the direction that the longitudinal axis of the seed is with respect to the ultrasound transducer; and 3) high voxel grey values produced by intra-prostatic calcifications or needle tracks.

Further, with the constraints of parallel trajectories, a re-plan may not provide the desired dose therapy with the fewest number of remaining needle insertions.

It is, therefore, an object of the present invention to provide a novel apparatus and computing device for performing brachytherapy and methods of imaging using the same.

SUMMARY OF THE INVENTION

In an aspect of the invention, there is provided an apparatus performing brachytherapy, comprising:

a robotic assembly having a needle guide for insertion of a brachytherapy needle into a patient, said robotic assembly being controllable to control the position and orientation of said needle guide in relation to said patient, said needle guide permitting manual longitudinal movement of said brachytherapy needle by an operator; and a computing device in communication with said robotic assembly, said computing device storing a dose distribution for a target volume and controlling said robotic assembly for positioning said needle guide in accordance with said dose distribution.

In accordance with another aspect of the invention, there is provided an apparatus for determining a distribution of a selected therapy in a target volume, comprising:

a three-dimensional ultrasound transducer for capturing volume data from said target volume; and a computing device in communication with said three-dimensional ultrasound transducer for receiving said volume data and determining said distribution of said selected therapy in said target volume along a set of planned needle trajectories using said volume data, at least one of said needle trajectories being oblique to at least one other of said planned needle trajectories.

In accordance with a further aspect of the invention, there is provided a computing device for determining a distribution of a selected therapy in a target volume, comprising:

FIGS. 9A and 9B show the difference map generated using the method of FIG. 8 before and after pre-filtration respectively;

a communications interface receiving volume data from a three-dimensional ultrasound transducer captured from a target volume;

a memory storing a dose distribution program; and a processor executing said dose distribution program for processing said volume data and determining said distribution of said selected therapy in said target volume along a set of planned needle trajectories using said volume data, at least one of said needle trajectories being oblique to at least one other of said planned needle trajectories.

In accordance with yet another aspect of the invention, there is provided an apparatus for segmenting seeds in a brachytherapy procedure, comprising:

a needle trajectory registrar for registering the trajectory of a brachytherapy needle in a target volume;

an ultrasound imaging device for imaging the trajectory of said brachytherapy needle in said target volume; and a seed segmenter for segmenting brachytherapy seeds implanted along the trajectory of brachytherapy needle.

In accordance with still yet another aspect of the invention, there is provided a method of segmenting seeds in a brachytherapy procedure, comprising:

imaging a target volume using three-dimensional ultrasound to locate a needle;

determining a trajectory for said needle using the location of said needle; and analyzing the target volume only along said trajectory to segment seeds implanted by said needle.

By considering oblique trajectories in determining a dosimetry for brachytherapy, the invention can reduce the number of "cold spots" in a target volume and can avoid anatomical features such as the pubic arch. By positioning a needle guide robotically, accurate manual placement of a brachytherapy needle along variably adjustable oblique trajectories can be provided. Using a priori knowledge of the trajectory of a brachytherapy needle, seeds can be more readily segmented in a target volume.

BRIEF DESCRIPTION OF THE DRAWINGS

Embodiments will now be described, by way of example only, with reference to the attached Figures, wherein.

DETAILED DESCRIPTION OF THE EMBODIMENTS

The use of oblique trajectories in determining a dosimetry provides a number of benefits. The number of needle insertions may be reduced in some cases. Where interference from the pubic arch and other anatomical structures, such as levator ani, the urethral sphincter, urethra and pained neurovascular bundles, is a concern, oblique trajectories and dosimetries using the same can provide desirable results.

Pubic arch interference ("PAI") with the implant path, however, occurs in many patients with large prostates and/or a small pelvis. These patients cannot be treated with current brachytherapy using parallel needle trajectories guided by a fixed template, because the anterior and/or the antero-lateral parts of the prostate are blocked by the pubic bone.

To solve the PAI problems, it is desirable to free needle insertions from parallel trajectory constraints. Oblique trajectories allow patients with PAI to be treated with brachytherapy without first undergoing lengthy hormonal downsizing therapy. In addition, changes in the prostate size prior to implantation, where the therapy is determined in advance of the procedure, and during the implantation, due to swelling of the prostate, may require re-optimization of the dose plan. The combination of precision 3D TRUS imaging, dosimetry and oblique needle insertion trajectories can provide the tools needed for dynamic re-optimization of the dose plan during the seed implantation procedure by allowing dynamic adjustments of the needle position to target potential "cold spots". Cold spots are areas more than a desired distance from seed implantation locations, resulting in less-than-desired exposure. Further, the dosimetry can be dynamically adjusted to compensate for deviations in the actual needle trajectories or shifting in the target volume.

While robotic insertion of a needle along an oblique trajectory is known, it is preferable in many cases to rely on manual insertion once the needle is positioned. Accurate seed segmentation permits accurate re-planning to complement the enhanced dosimetry planning.

Figure 1:
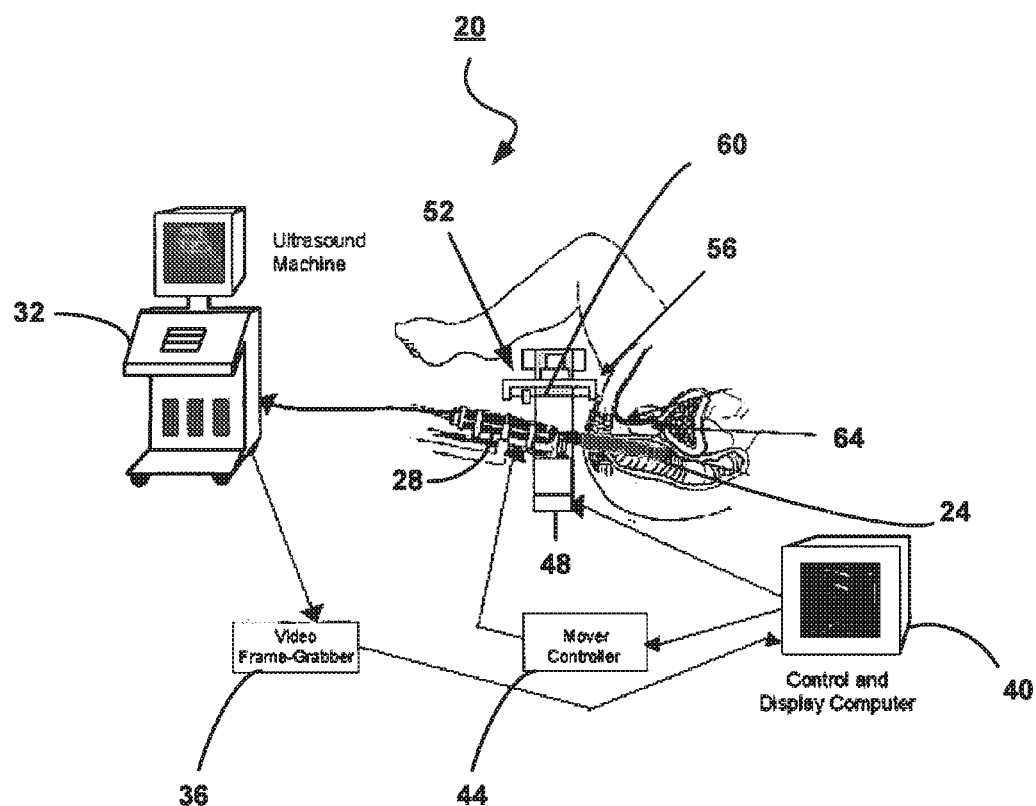
FIG. 1 is a schematic diagram of an ultrasound imaging system for imaging a target volume in a subject.

A 3D TRUS-guided robot-aided prostate brachytherapy system is shown generally at 20 in FIG. 1. The system 20 includes a TRUS transducer 24 coupled to a motor assembly 28 that operates to control the longitudinal movement and rotation of the TRUS transducer 24. The TRUS transducer 24 is also coupled to a conventional ultrasound machine 32 for displaying image data as it is captured by the TRUS transducer 24. A video frame-grabber 36 is connected to the ultrasound machine 32 to capture image data therefrom. The video frame-grabber 36 preferably operates at 30 Hz or greater to provide rapidly updated ultrasound images.

A computer 40 is connected to the video frame-grabber 36 and retrieves ultrasound images from the memory of the video frame-grabber 36. The computer 40 is coupled to a mover controller module ("MCM") 44 that is coupled to and controls the motor assembly 28. The computer 40 is also connected to the TRUS transducer 24. Further, the computer 40 is connected to a robot 48 having a robotic arm 52 with a needle guide 56 for controlling movement of a needle 60. The needle guide 56 is a one-holed template used to stabilize lateral movement of the needle 60 during insertion and permitting longitudinal and rotational movement of the needle 60. The needle 60 is used to deliver therapy to a prostate 64 of a patient. The robot 48 receives needle control commands from and transmits needle position information to the computer 40.

The TRUS transducer 24 is operable to continuously capture radial 2D US images over a radial operational scan range. The MCM 44 which controls the TRUS transducer 24 is in communication with the computer 40 to receive TRUS control commands via the serial port of the computer 40. The TRUS control commands direct the MCM 44 to control the motor assembly 28. In turn, the motor assembly 28 controls the longitudinal movement and rotation of the TRUS transducer 24. Additionally, the TRUS control commands control the timing of image data capture of the TRUS transducer 24.

The robot 48 includes a robotic arm with five degrees-of-freedom. The degrees-of-freedom correspond to translations of the needle guide 56 in three dimensions and rotation of the needle guide 56 about two orthogonal axis that are, in turn, orthogonal to the needle guide 56. In this manner, the needle 60 inserted in the needle guide 56 can be positioned in a wide variety of orientations.

The computer 40 is a personal computer having a processor that executes software for performing 3D image acquisition, reconstruction and display. The processor also executes software for determining dosimetry of a selected therapy, and for controlling the TRUS transducer 24 and the robot 48. The software executed by the processor includes TRUS controller software, positioning software, imaging software, 3D visualization software and dose planning software.

The TRUS controller software generates TRUS control commands for directing the MCM 44, thereby controlling the longitudinal and rotational movement and the image data acquisition timing of the TRUS transducer 24.

The positioning software generates needle control commands to control movement of the robotic arm 52 of the robot 48. The positioning software can direct the robotic arm 52 to move in terms of world or tool coordinate systems. The world coordinate system is fixed to the ground, whereas the tool coordinate system is fixed to the robotic arm.

The imaging software captures, analyzes and processes ultrasound images using the image data retrieved from the memory of the video framegrabber 36. The positioning software provides needle position information using the selected coordinate system. In turn, the imaging software directs the TRUS controller software to vary the operation of the TRUS transducer 24 as will be explained.

The 3D visualization software renders 3D images to be presented on a display (not shown) of the computer 40 using the image data captured and processed by the imaging software. In particular, the 3D visualization software generates three orthogonal views of the target volume: two that are co-planar to the needle 60 and a third that generally bisects the trajectory of the needle 60.

The dose planning software performs precise image-based needle trajectory planning. In addition, the dose planning software provides planned needle trajectory information to the 3D visualization software so that the planned needle trajectory can be overlaid atop the US images on the display. The actual needle trajectory can then be viewed in relation to the planned needle trajectory.

The dose planning software can also receive and process the US images from the imaging software and dynamically re-determine the dosimetry based on the actual needle trajectory and seed implantation locations.

Prior to use, the positioning software controlling movement of the robot 48, the needle driving assembly 52 and, thus, the needle 60, and the imaging software are calibrated. During calibration, the mapping between the selected coordinate system of the positioning software and the 3D TRUS image coordinate system is determined and synchronized. In this manner, the imaging software can be made aware of the expected position of the needle 60 before detection via imaging.

By unifying the robot 48, the TRUS transducer 24 and the 3D TRUS image coordinate systems, the position of the template hole of the needle guide 66 can be accurately related to the 3D TRUS image coordinate system, allowing accurate and consistent insertion of the needle via the hole into a targeted position in a prostate along various trajectories including oblique ones. Further, the operation of the TRUS transducer 24 can be varied to focus its attention on the expected position of the needle 60.

Figure 2:
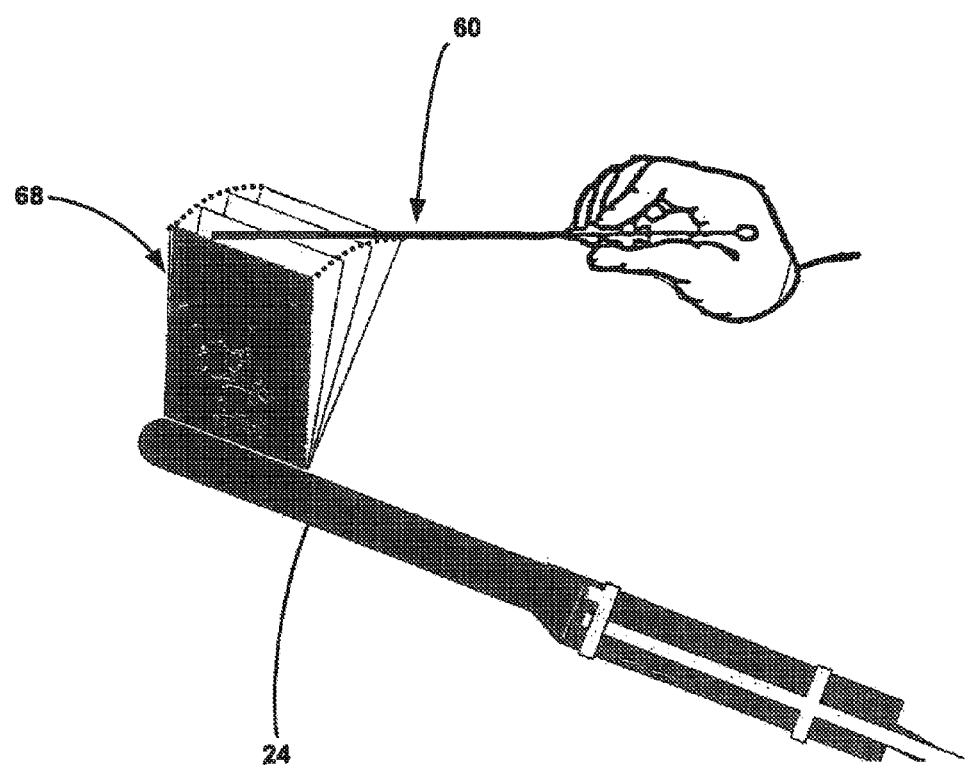
FIG. 2 shows a three-dimensional ("3D") TRUS transducer forming part of the ultrasound imaging system of FIG. 1 capturing a set of 2D US images of a needle.

FIG. 2 shows the 3D TRUS transducer 24 capturing a set of 2D US images. As the TRUS transducer 24 is rotated by the MCM 44, it captures image data to generate a series of 2D images 68. The 2D images 68 are captured at generally regular intervals during rotation of the TRUS transducer 24. Initially, the TRUS transducer 24 captures a 2D image 68 every one degree of rotation and rotates through 100 degrees, thereby capturing one hundred and one 2D images 68. The captured 2D images 68 are fanned radially in relation to the TRUS transducer 24. The needle 60 is shown having an oblique trajectory in relation to the 2D images 68, and intersects two or more of the 2D images 68. The 2D images in combination comprise a 3D volume data.

As will be understood, insertion of the needle 60 along an oblique trajectory results in the intersection of the 2D TRUS image planes. As a result, the needle 60 only appears as a point in the captured 2D US images.

Figure 3A:
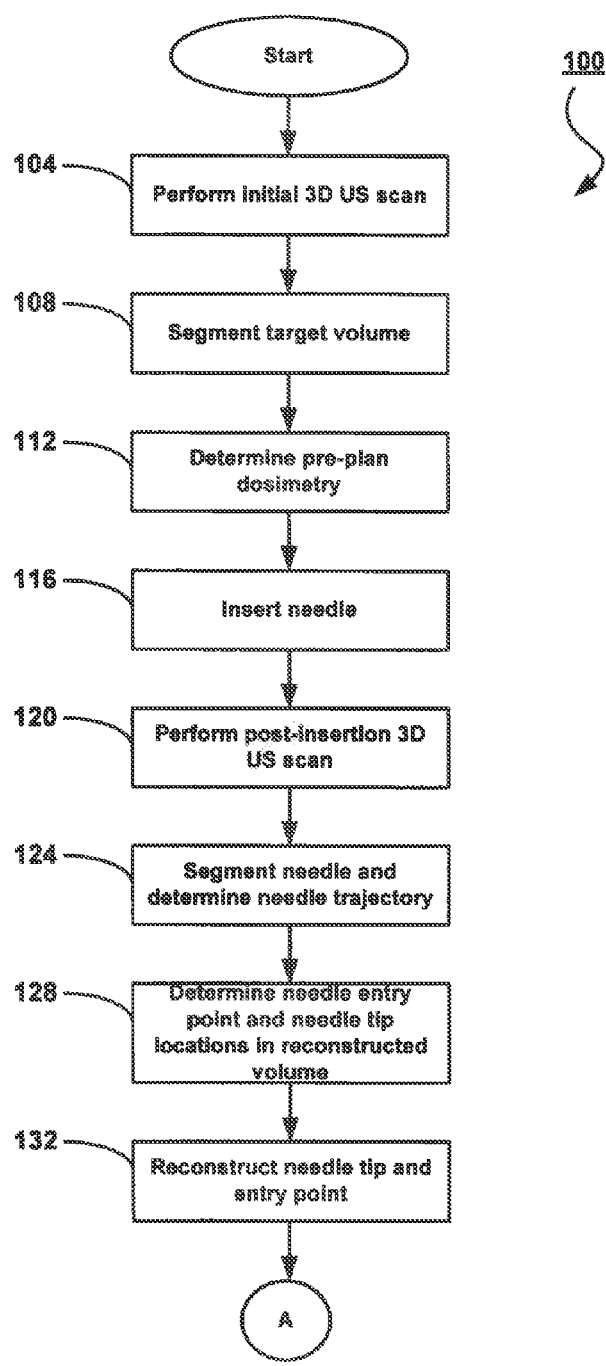
FIGS. 3A and 3B are flow charts of the general method of operation of the system of FIG. 1.
Figure 3B:
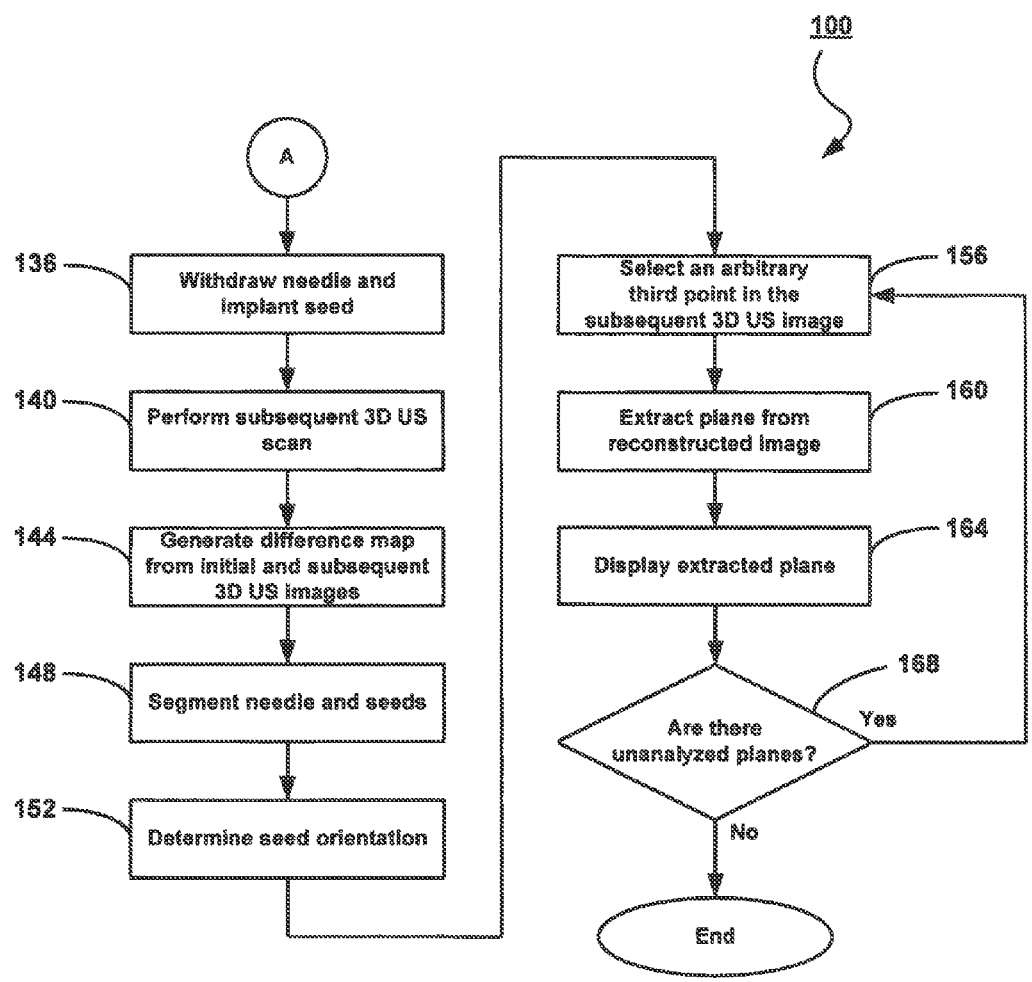

A near real-time method 100 for identification, segmentation and tracking of the needle 60 and seeds will now be described with reference to FIGS. 3A and 3B. The method 100 enables the tracking of the needle 60 even if the needle 60 is not coplanar and, thus, exits a 2D US image plane as a result of an oblique insertion. The method can also be used for the identification, segmentation and tracking of needles if they are completely contained in a 2D US image plane. A 3D US image is comprised of two or more 2D US images that are offset.

The initial 3D US image is obtained by scanning the prostate (tissue) to obtain a set of 2D US images before the needle and seeds are inserted. This 3D US image establishes a baseline or control against which other images will be compared. A post-insertion 3D US image is then acquired by scanning only the region containing the needle. The method, as described, is used to identify, segment and track the needle 60 and any implanted seeds in each subsequent 3D US image captured after the first 3D US image is captured. Each new 3D US image is compared to the initial image to identify the position of newly-implanted seeds.

The method 100 commences with the performance of an initial 3D US scan (step 104). The target volume (i.e., the prostate) is segmented (step 108). A pre-plan dosimetry is determined for the target volume (step 112). The needle 60 is then inserted into the target volume (step 116). Next, a post-insertion 3D US scan is performed (step 120). The needle 60 is segmented to distinguish its location using the initial and post-insertion 3D US images and the needle trajectory is then determined (step 124). Once the needle trajectory has been determined, the needle tip and needle entry point locations within the reconstructed volume are determined (step 128). The needle tip and entry point locations are then reconstructed (step 132). As the needle is withdrawn, seeds are implanted (step 140). A difference map is generated from the initial and subsequent 3D US image (step 144). The needle and seeds are segmented from the difference map (step 148). The orientation of segmented seeds is determined (step 152). An arbitrary third point in the target volume is selected (step 156). The plane defined by the needle tip and entry points and the arbitrary third point is extracted from the reconstructed 3D image (step 160). Next, the extracted plane is displayed (step 164). It is then determined if there are any remaining unanalyzed planes (step 168). If there are, the method 100 returns to step 156, at which another arbitrary point is selected. If, instead, all of the desired planes have been analyzed, the method 100 ends.

During the performance of the initial 3D US scan at step 104, the MCM 44 and motor assembly 28 causes the TRUS transducer 24 to rotate about its long axis over about 100 degrees while image data corresponding to 2D US images is captured at one degree intervals. The image data corresponding to the 2D US images is then transmitted to the computer 40 to be digitized by the video frame grabber 36 and registered by the imaging software. The acquired 2D US images are processed by the imaging software as they are collected. The 2D US images correspond to planes radially extending from the central axis of rotation of the TRUS transducer 24. Accordingly, the 3D volume is reconstructed by translating and rotating the 2D US images with respect to one another. The reconstructed 3D volume consists of an array of voxels, or 3D pixels. The voxels are typically cubic (but can also be rhomboidal) and are arranged according to a 3D Cartesian system. Each voxel is assigned a greyscale-level value based on the greyscale-level values of the pixels in the translated 2D images adjacent to it.

Figure 4:
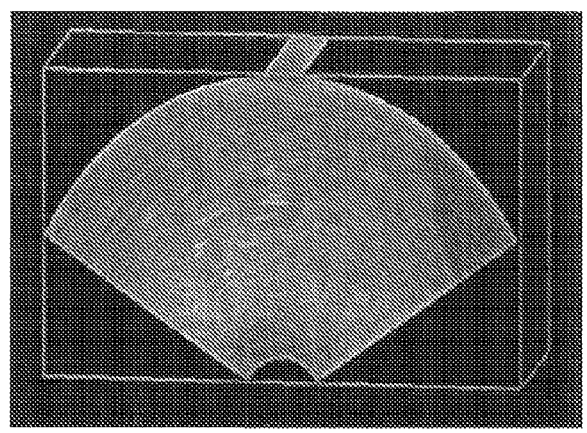
FIG. 4 shows a reconstructed 3D image generated from 2D ultrasound images captured by the TRUS transducer shown in FIG. 2.

FIG. 4 illustrates a 3D US image reconstructed from the set of 2D US images. As can be seen, the 3D US image has a fan profile corresponding to the volume imaged by the TRUS transducer 24. The acquired 2D US images are reconstructed into a 3D US image by the imaging software. The 3D visualization software then generates a view of the 3D US image, and provides a multi-planar 3D display and volume rendering, as well as an extensive set of measurement tools. The 3D US image is then presented for viewing on the display of the computer 40. As each new 2D US image is acquired by the TRUS transducer 24 during its rotation, the 3D visualization software dynamically updates the 3D image presented on the display.

Figure 5:
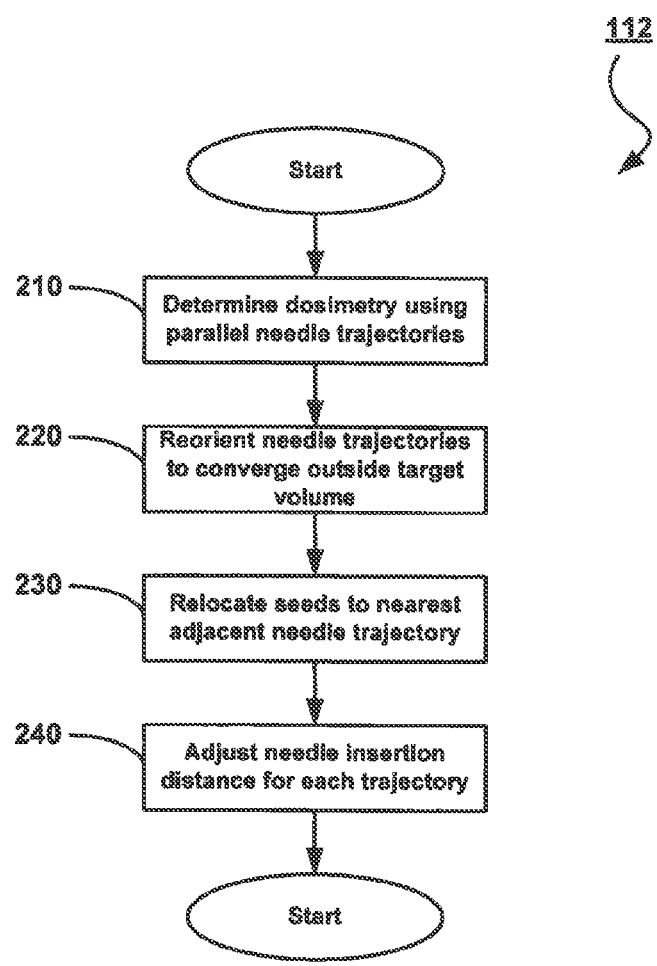
FIG. 5 is a flow chart illustrating the method of performing a pre-plan using oblique needle trajectories.

During the segmentation of the target volume at step 108, the limits of the target volume are determined and registered. This information is then provided to the dose planning software. The determination of a pre-plan dosimetry by the dose planning software at steps 112 will now be described with reference to FIG. 5.

As the prostate has an inverted, generally frustoconical shape, it has been found that a fanned distribution of needle trajectories provide a desirable basis for a dosimetry.

The method of determining a pre-plan dosimetry commences with the determination of a dosimetry using parallel needle trajectories (step 210). The planned needle trajectories are reoriented to converge outside the target volume (step 220). The seed locations determined at step 210 are relocated to adjacent needle trajectories (step 230). The needle insertion distances are then adjusted for each trajectory (step 240).

During the reorientation of the needle trajectories at step 220, the tips of the needle trajectories are fixed and the trajectory is converged to avoid anatomical features at the base of the prostate.

After the initial and post-insertion 3D US scans have been completed, the needle 60 is segmented at step 124. The post-insertion 3D US image is compared to the initial 3D US image, and the needle position within the post-insertion 3D US image, including the needle tip and entry point location, is determined. The needle 60 will show up as voxels with a greyscale-level change that exceeds a threshold value between the initial and post-insertion 3D US images. There can be, however, other voxels with a greyscale-level change that exceeds the threshold value that do not, in fact, represent the needle, but may represent, for example, calcifications in the prostate. In order to permit better identification of the actual needle, the system 20 attempts to identify and discard these other voxels.

Figure 6:
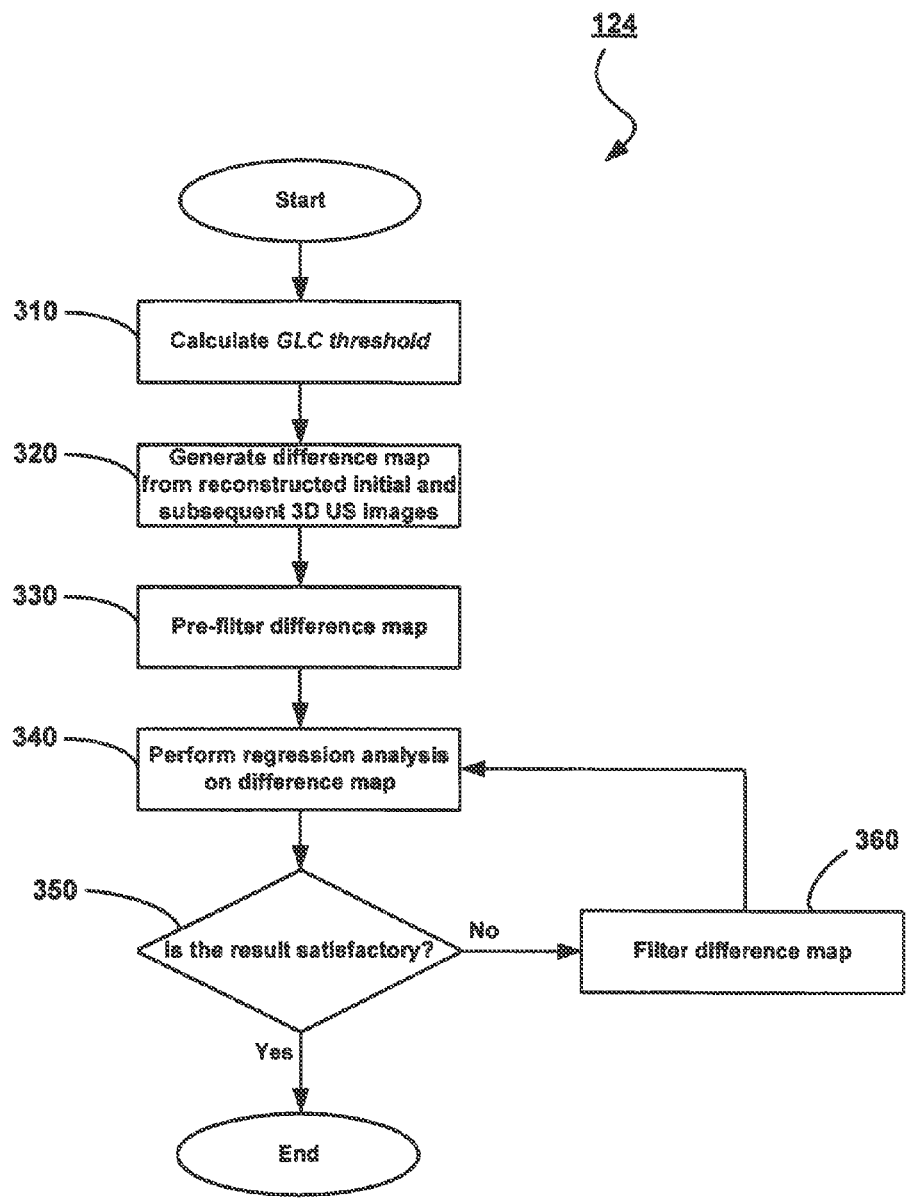
FIG. 6 is a flow chart that illustrates the method of segmenting a needle.

FIG. 6 better illustrates the method of needle segmentation at step 116. The method commences with the calculation of a greyscale-level change threshold (step 310). A difference map is then generated from the initial and post-insertion 3D US images (step 320). Next, the difference map is pre-filtered (step 330). Regression analysis is performed on the difference map to identify the needle (step 340). The result of the regression analysis is then analyzed to determine if it is satisfactory (step 350). If the results are determined to be unsatisfactory, the difference map is filtered (step 360), and the method returns to step 340, where regression analysis is again performed on the filtered image. The filtering of the difference map and the regression analysis is repeated until all of the voxels in the difference map are within a prescribed range from the regression line. As the filtering removes outlying voxels, their effect on the linear regression is removed, thereby allowing the needle trajectory to be more accurately estimated. Reiterative filtration of the difference map is performed to obtain a desired level of confidence in the estimated needle trajectory. Once the result of the regression analysis is deemed to be satisfactory at step 350, the method ends.

Figure 7:
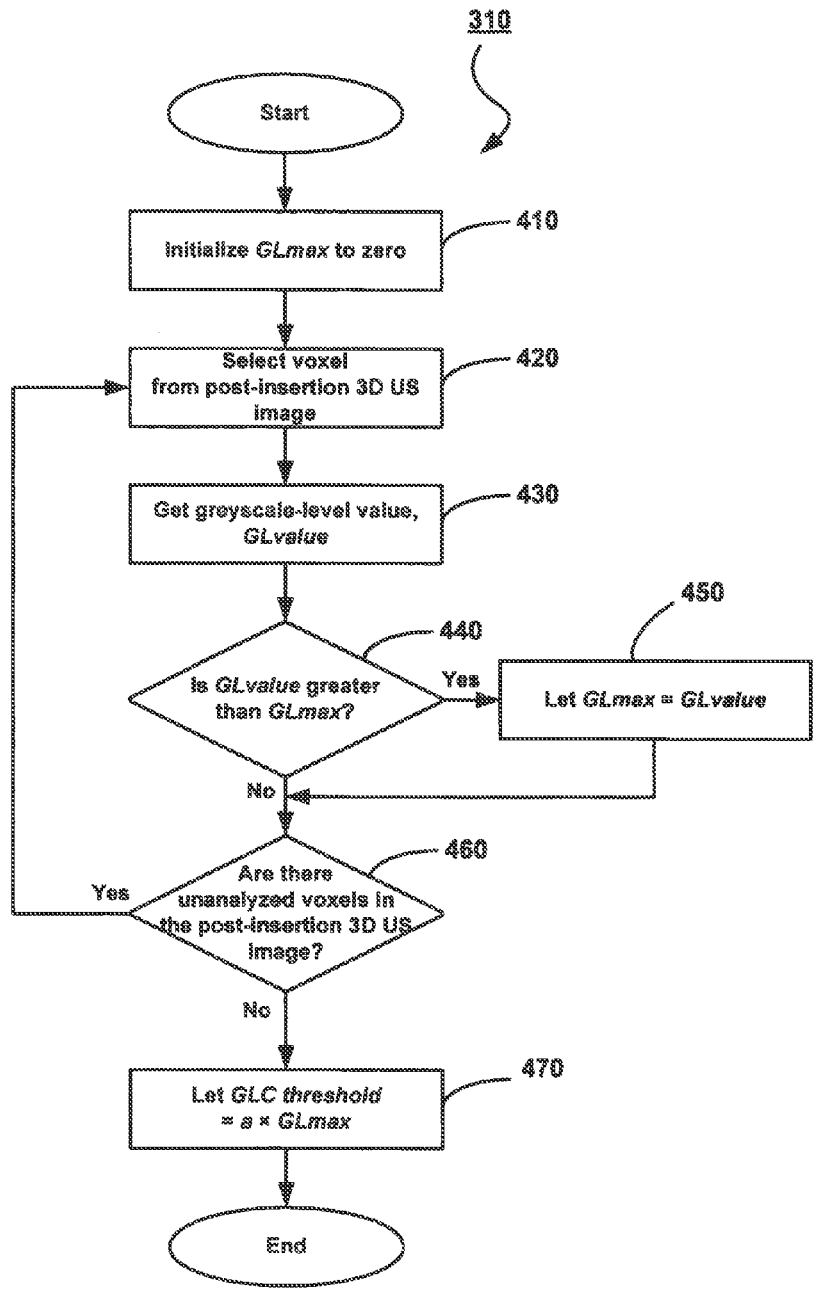
FIG. 7 is a flow chart that illustrates the method of determining the greyscale-level change threshold.

FIG. 7 better illustrates the calculation of the greyscale-level change threshold at step 310. A greyscale-level change threshold value, GLC threshold, is used to reduce the number of voxels to be analyzed in the 3D US images and to obtain candidate needle voxels. To determine the threshold value, the maximum grayscale-level value, $GL_{max}$, in the post-insertion 3D US image is first determined by examining each voxel in the image, and then $GL_{max}$ is multiplied by a constant.

The calculation of GLC threshold commences with the setting of $GL_{max}$ to zero (step 410). A voxel is then selected from the post-insertion 3D US image (step 420). The greyscale-level value, $GL_{value}$, of the selected voxel is determined (step 430). The greyscale-level value of the selected voxel, $GL_{value}$ is then compared to the maximum greyscale-level value, $GL_{max}$ (step 440). If the greyscale-level value of the selected voxel, $GL_{value}$, is greater than the maximum greyscale-level value, $GL_{max}$, the value of $GL_{max}$ is set to $GL_{value}$ (step 450). It is then determined whether there are any unanalyzed voxels remaining in the post-insertion 3D US image (step 460). If there are, the method returns to step 420, where another voxel is selected from the post-insertion 3D US image. If, instead, it is determined at step 460 that there are no remaining unanalyzed voxels in the post-insertion 3D US image, the greyscale-level change threshold value is calculated as follows:

$$GLC\ threshold = a \times GL_{max} \qquad (Eq.\ 1)$$

where $0<a<1$. A value for a of 0.5 provides desirable results.

Figure 8:
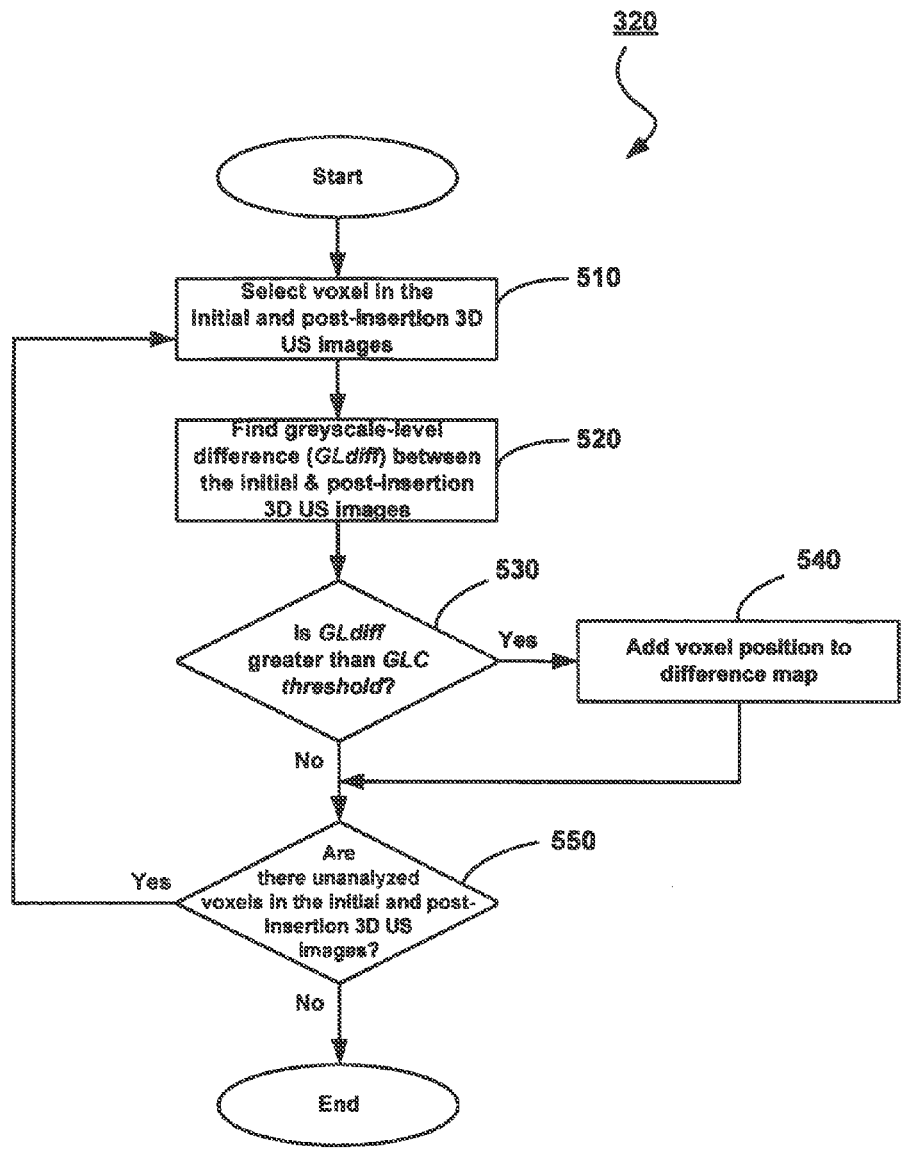
FIG. 8 is a flow chart that illustrates the method of generating a difference map.

FIG. 8 better illustrates the generation of a difference map during step 320 using the threshold calculated during step 310. The difference map is a registry of candidate needle voxels that represent an area of the same size as the initial and post-insertion 3D US images. Initially, the greyscale-level value of each voxel in the initial 3D US image is compared to that of its counterpart in the post-insertion 3D US image, and the difference is determined:

$$GLC(i,j,k) = postGL(i,j,k) - preGL(i,j,k) \qquad (Eq.\ 2)$$

where $preGL(i,j,k)$ and $postGL(i,j,k)$ are the greyscale-level values of voxels at location $(i,j,k)$ in the initial and post-insertion 3D US images respectively, and $GLC(i,j,k)$ is the greyscale-level change.

Those voxels in the post-insertion 3D US image whose greyscale-level values exceed those of their counterpart in the initial 3D US image are deemed to have changed significantly and are registered in the difference map. That is, $$(i_m, j_m, k_m) \in 3D\ DM,\ \text{where}\ GLC(i_m, j_m, k_m) > GLC\ threshold \qquad (Eq.\ 3)$$

for m=1, 2, . . . , n, where n is the number of points included in the 3D difference map. The remaining voxels having greyscale-level values that do not exceed those of their counterpart in the initial 3D US image are deemed to have changed insignificantly and are not added to the difference map.

The method of generating the difference map begins with the selection of a voxel in the post-insertion 3D US image and its counterpart in the initial 3D US image (step 510). The greyscale-level difference, GLdiff, between the voxels of the initial and post-insertion 3D US images is found (step 520). The greyscale-level difference, GLdiff, is compared to the greyscale-level change threshold, GLC threshold, to determine if it exceeds it (step 530). If it is determined that the greyscale-level difference, GLdiff, exceeds the greyscale-level change threshold, GLC threshold, the position of the voxel is added to the difference map (step 540). It is then determined whether there are any remaining unanalyzed voxels in the initial and post-insertion 3D US images (step 550). If it is determined that there are unanalyzed voxels remaining in the initial and post-insertion 3D US images, the method returns to step 510, where another pair of voxels is selected for analysis. If, instead, it is determined that all of the voxels in the initial and post-insertion 3D US images have been analyzed, the method of generating the difference map ends.

During pre-filtration of the difference map at step 330, voxels registered in the difference map are analyzed to remove any voxels that are deemed to be noise. In the system 20, the 3D image is advantageously reconstructed on demand and, therefore, access to the original acquired image data is available.

Voxels are identified and analyzed to determine whether they correspond to a characteristic of the needle. Since the image of the needle is expected to extend along the 3D scanning direction, voxels representing the needle are assumed to be generally adjacent each other along this direction. Other voxels in the difference map that are more than a pre-determined distance along this direction from other voxels are deemed to be noise and removed. That is, assuming that k is the direction along which the needle is expected to extend, voxels are removed from the difference map as follows:

$$(i_m, j_m, k_m) \notin 3DDM, \qquad (Eq.\ 4)$$
$$\text{where}\ \bigcup_{m=1}^{P} GLC(i_m, j_m, k_m \pm s) < GLC\ threshold$$

where, s=1, 2, . . . , $^P I_2$, and P is the number of voxels surrounding voxel $(i_m, j_m, k_m)$ in the k-direction. A value for P of 4 provides desirable results.

Figure 9A:
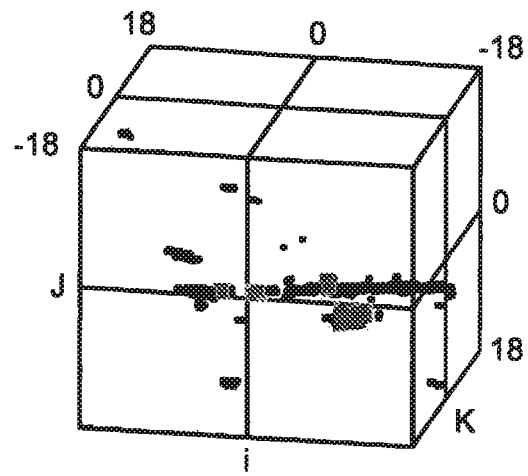
FIGS. 9A and 9B show the difference map generated using the method of FIG. 9 before and after pre-filtration respectively.
Figure 9B:
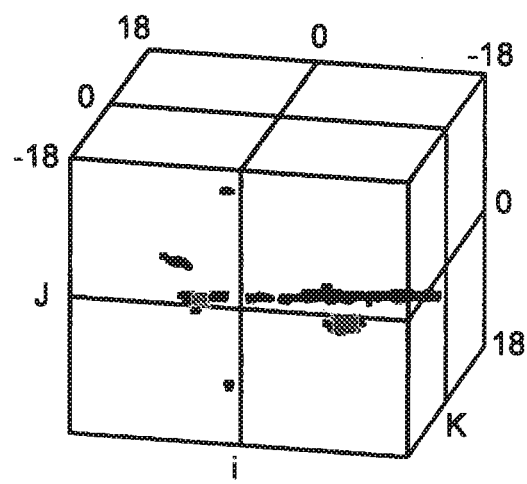

FIGS. 9a and 9b show the difference map prior to and after pre-filtration respectively. As can be seen, spurious voxels not occurring in clusters extending along the same path as the needle are removed during pre-filtration.

Once the difference map has been pre-filtered, regression analysis is performed on the difference map at step 340. During this analysis, a line is fit to the voxels in the difference map using linear regression analysis. The equation of the line determined from the difference map using linear regression analysis provides the estimated trajectory for the needle.

Figure 10:
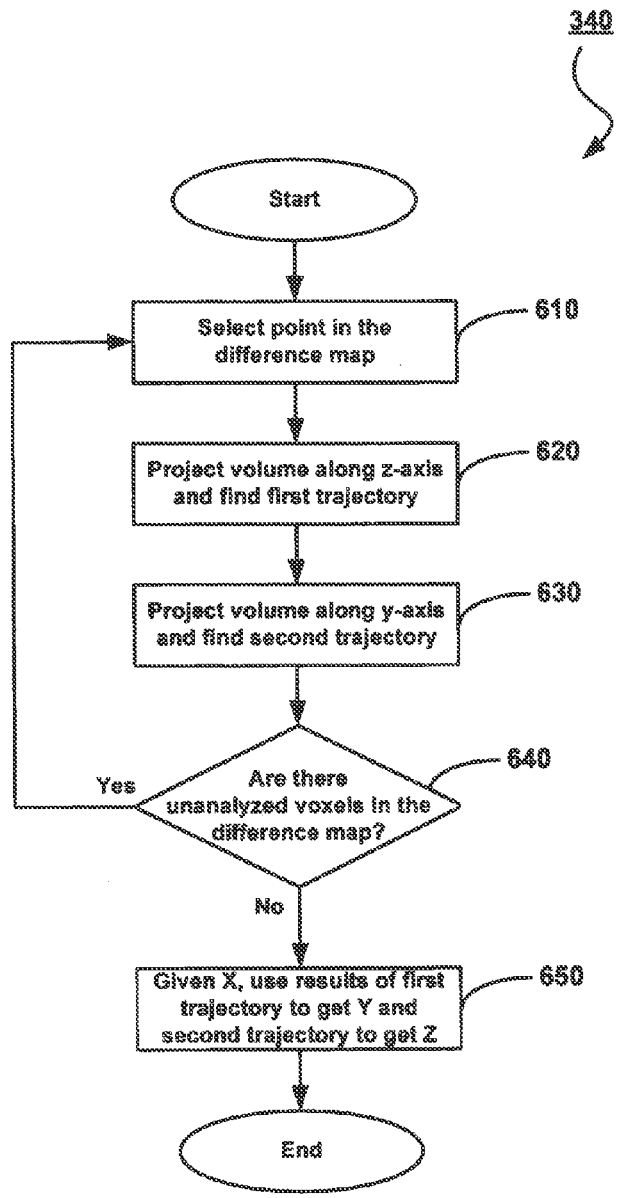
FIG. 10 is a flow chart that illustrates the method of performing regression analysis.

FIG. 10 better illustrates the performance of the regression analysis on the difference map at step 340. A voxel registered in the difference map is selected (step 610). The volume is projected along the z-axis to find a first trajectory (step 620). Next, the volume is projected along the y-axis to find a second trajectory (step 630). It is then determined if there are any unanalyzed voxels in the difference map (step 640). If it is determined that there are unanalyzed voxels in the difference map, the method returns to step 610, where another voxel is selected in the difference map for analysis. If, instead, all of the voxels in the difference map have been analyzed, the results of the first trajectory are used to obtain y and the results of the second trajectory are used to obtain z, given x (step 650). Once (x,y,z) has been determined, the method 240 ends.

If it is determined at step 350 that the linear regression is unsatisfactory, the difference map is filtered at step 360.

Figure 11:
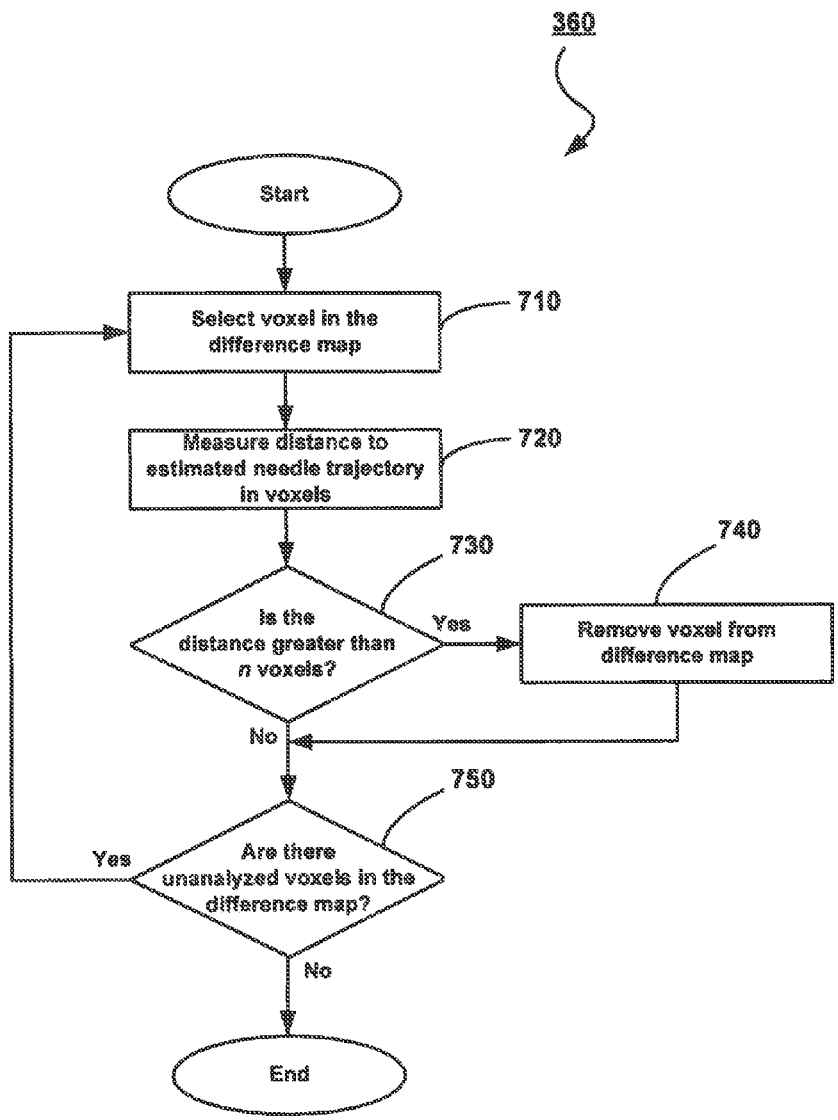
FIG. 11 is a flow chart that better illustrates the method of filtering the difference map.

FIG. 11 better illustrates the filtering of the difference map. During the filtering of the difference map, spurious voxels that are further than a pre-determined distance from the estimated trajectory of the needle determined during step 340 are removed.

The method of filtering the difference map commences with the selection of a voxel in the difference map (step 710). The distance to the estimated needle trajectory is measured in voxels (step 720). A determination is then made as to whether the distance between the voxel and the estimated needle trajectory is greater than a predetermined distance limit (step 730). It has been found that filtering out voxels further than five voxels in distance from the segmented needle trajectory provides desirable results. If the distance determined is greater than the pre-determined distance limit, the voxel is removed from the difference map (step 740). Then, it is determined if there are any unanalyzed voxels remaining in the difference map (step 750). If there are, the method returns to step 710, wherein another voxel in the difference map is selected for analysis. If, instead, all of the voxels in the difference map have been analyzed, the method of filtering the difference map ends.

Figure 12:
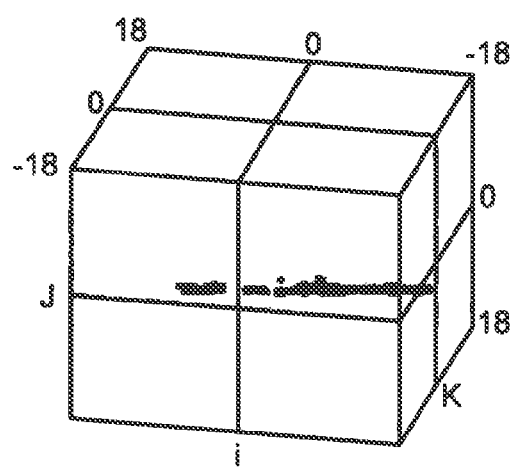
FIG. 12 shows the difference map of FIGS. 9A and 9B immediately prior to the performance of the final regression analysis.

FIG. 12 shows the difference map of FIGS. 9*a* and 9*b* after filtration at step 360 and immediately prior to the final regression calculation. As can be seen, the difference map is free of spurious voxels distant from the visible needle trajectory.

As mentioned previously, once the needle trajectory has been determined, the needle entry point and needle tip locations are determined in the reconstructed volume at step 124. The needle entry point is determined to be the intersection of the needle trajectory and the known entry plane. The needle tip is deemed to be the furthest needle voxel along the needle trajectory.

Once the needle 60 has been segmented, the needle 60 is withdrawn along the trajectory and one or more seeds are implanted. As the seeds exit the tip of the needle, they expected to remain along the trajectory.

During the performance of the subsequent 3D US scan at step 140, a region of interest is identified, and the ultrasound imaging system 20 is focused on a segment of an operational scan range of the TRUS transducer encompassing the region of interest in a target volume. In particular, the TRUS transducer is focused on the segment to capture images of the expected position of the needle 60.

As the needle 60 withdraws from the prostate, spacing is created between the needle 60 and the implanted seeds. The isolation of the seeds allow them to be segmented. As the tip of the needle 60 moves out of the target volume, it is monitored to detect newly-implanted seeds.

Figure 13:
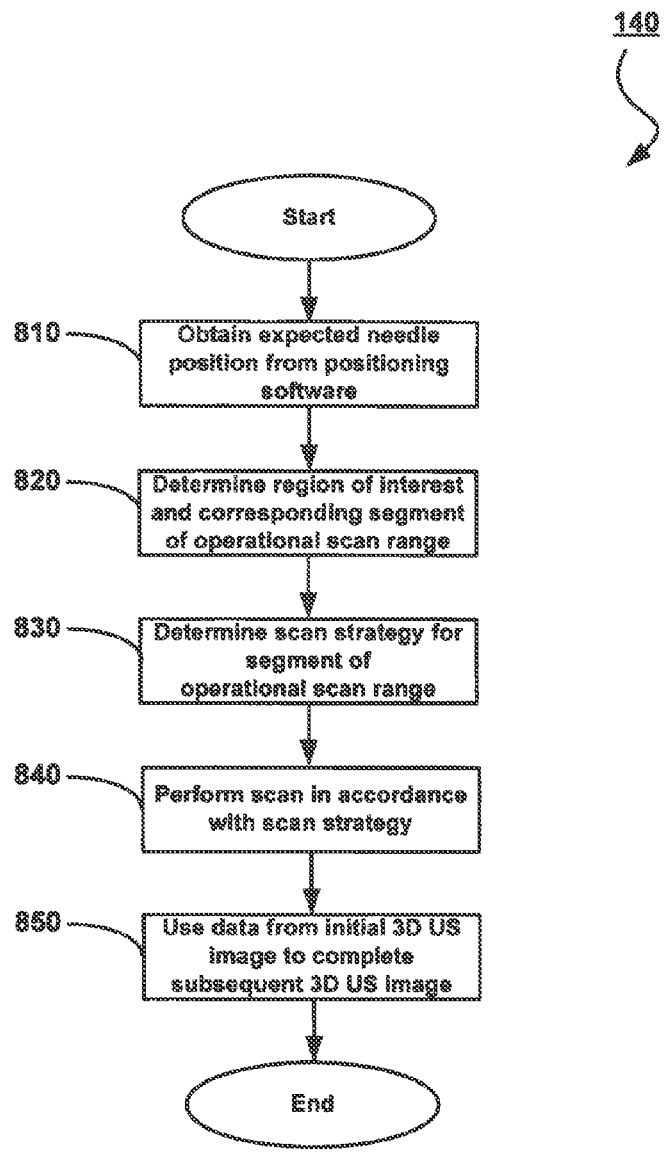
FIG. 13 is a flow chart illustrating the method of performing a subsequent 3D US scan.

FIG. 13 better illustrates the performance of the subsequent 3D US scan at step 140. The expected needle position is obtained from the positioning software (step 810). The region of interest is determined based on the expected position of the needle, and a corresponding segment of the operational scan range of the TRUS transducer 24 is determined (step 820). Next, a scan strategy for the segment of the operational scan range is determined (step 830). In determining the scan strategy for the segment of the operational scan range at step 830, the positions of 2D US images to be acquired is determined. In particular, a set of 2D US images are planned at one-half degree intervals along the angular width of the scan region of interest. A scan is then performed in accordance with the scan strategy (step 840). Data from the initial 3D US image is then used to complete the 3D US image (step 850).

During the determination of the region of interest at step 820, the region of interest is selected to include the expected needle position obtained during step 810. Portion of the needle trajectory from just beyond the tip to about one-half of one inch down the length of the needle from the tip.

The region of interest is then reverse-mapped onto the operating coordinates of the TRUS transducer 24 and is used to determine a segment of the operational scan range of the TRUS transducer 24 that encompasses the region of interest at step 230. In particular, the segment of the operational scan range is selected to correspond to an angular sector of the operational scan range of the TRUS transducer 24 that encompasses the region of interest. Where the needle is inserted along an oblique trajectory and, consequently, intersects a number of 2D US images at points, the angular width of the sector is selected to sufficiently cover the region of interest plus five degrees of rotation to cover the distance along the needle trajectory beyond the needle tip.

Figure 14:
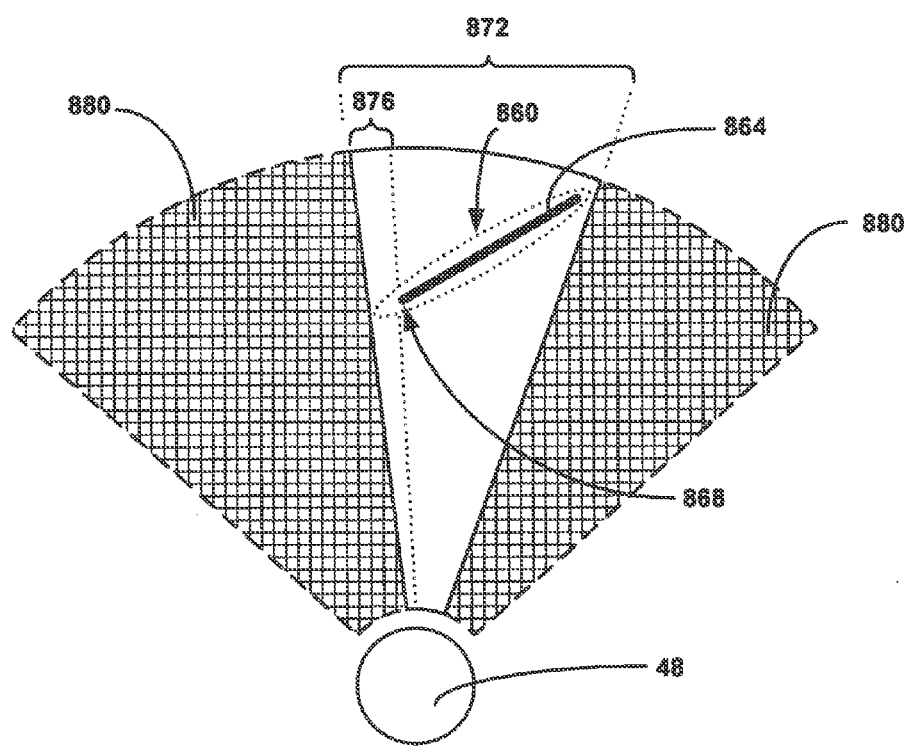
FIG. 14 is a sectional view of a scan range corresponding to a region of interest determined using the method of FIG. 13.

FIG. 14 is an end-view of the TRUS transducer 24 and the segment of the operational scan range selected during step 820 for the needle when it is inserted along an oblique trajectory. A region of interest 860 encompasses the entire inserted needle length 864 and extends a distance past the needle tip position 868 at full insertion. A segment of the operational scan range 872 corresponding to the sector encompasses the region of interest 860. The segment of the operational scan range 872 includes a five-degree margin 876 to capture the region of interest extending along the needle trajectory beyond the needle tip position 868 at full insertion. Two background areas 880 of the operational scan range of the TRUS transducer 24 flank either side of the sector.

During the completion of the subsequent 3D US image at step 850, data from the initial 3D US image is used to fill in the background areas. As the scan strategy can exclude the capture of some or all image data from the background areas, image data from the initial 3D US scan is used to fill in any image data required in the subsequent 3D US image. The image data in the background areas is not expected to change and can, thus, be borrowed from the initial 3D US image.

By modifying the behavior of the TRUS transducer 24 to focus on the region of interest, more detailed information can be captured around the needle 60 on a near real-time basis. Further, by reducing the scanning density for the other areas, the additional time required to scan the region of interest can be compensated for.

During the generation of a difference map at step 144, a subsequent 3D US image is compared to the initial 3D US image.

During the segmentation of the needle 60 and the seeds at step 148, the same general method is used as for the segmentation performed at steps 124. The difference map is thresholded to identify candidate needle and seed voxels. Connected candidate needle and seed voxels are clustered. Each of these clusters is further analyzed to see if they represent a seed. Clusters with small number of connected voxels are given a low probability of being a seed and can be removed from the list. The knowledge of the needle location received from the positioning software is used to eliminate those clusters with a high probability of representing the needle. Other tests (such as for size matching) can be performed on these groups to identify whether or not they represent seeds. The clusters of seed candidate voxels with the highest probability of being a seed are kept and the rest discarded. Each seed candidate voxel cluster that is left in the list is assumed to be a seed.

To find the center and approximate orientation of the seed at step 152, a linear regression is performed on each cluster and the trajectory or orientation of the seed is determined. The result of the linear regression is used to find the end points and center of the seed.

An arbitrary third point in the subsequent 3D US image is selected at step 156. To extract any plane containing the needle and seeds, the segmented needle entry point, needle tip point and a third point within the subsequent 3D US image are used to define a specific plane that is coplanar with the needle (i.e., contains the needle lengthwise). The location of the arbitrary point determines whether the plane will be sagittal-oblique or coronal oblique. For a sagittal-oblique plane, the arbitrary point is picked on a line going through the needle entry point and parallel to the y-axis. For a coronal-oblique plane, the arbitrary point is picked on a line going through the needle entry point and parallel to the x-axis.

The data occurring along the plane in the 3D US image is extracted at step 160 to permit generation of a 2D US image of the plane. In this way, the oblique sagittal, coronal and transverse views with the needle highlighted can be extracted and displayed.

Once the plane is extracted, the 2D US image of the plane is presented on the display of the computer 40 at step 164. The location of the needle 60 in the 2D US image is demarcated using a colored line in the greyscale image to facilitate visual identification of the needle.

It is then determined whether there remain any unanalyzed planes at step 168. As three planes are displayed by the computer 40 at the same time, the process is repeated twice to obtain the other two planes. The first plane selected for analysis is the sagittal plane and the other two planes are orthogonal to the first plane. If there are, the method returns to step 156, where another arbitrary point is selected to define another plane. Otherwise, the method 100 ends.

Figure 15A:
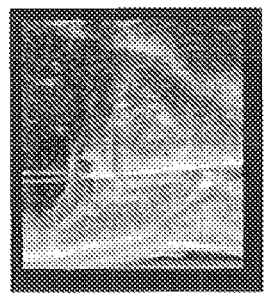
FIGS. 15A to 15C show various 2D US images generated using the ultrasound imaging system of FIG. 1.
Figure 15B:
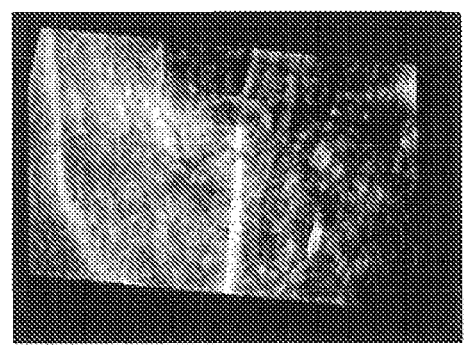
Figure 15C:
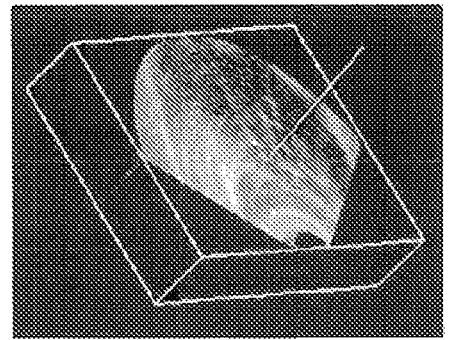

FIGS. 15a to 15c show a 2D US image obtained using the method 100 during a patient's prostate cryotherapy procedure, demonstrating that the needle can be tracked as it is being inserted and orthogonal views can be displayed for the user during the insertion procedure.

Figures 16A, 16B:
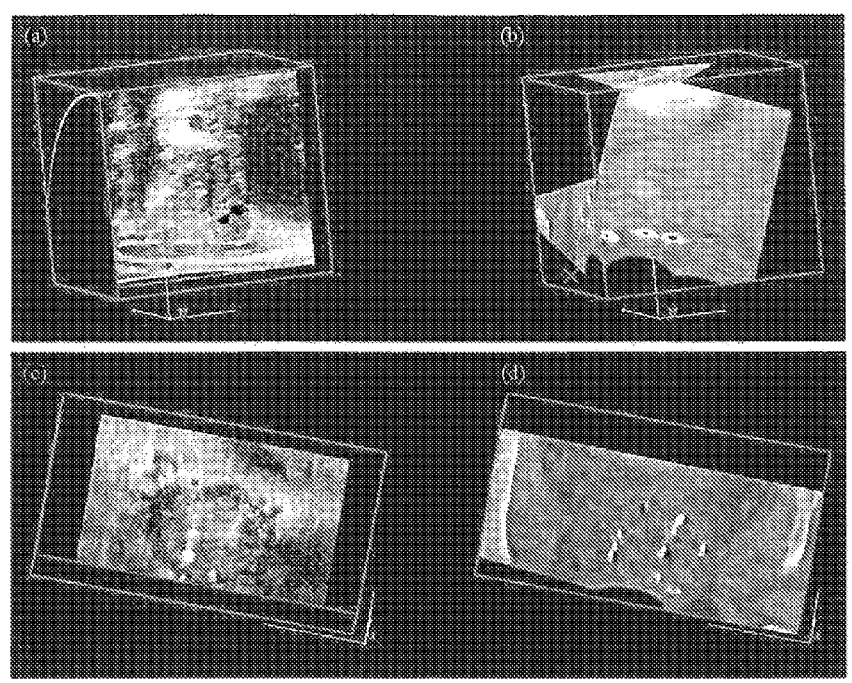
FIGS. 16A and 16B show the seed segmentation performed using the system of FIG. 1.

FIGS. 16A and 16B illustrate segmented seeds as detected using the system 20 on the left and using CT on the right.

Alternative Methods of Seed Segmentation

Another method of segmenting seeds using a priori information about the location of the needle is disclosed. This seed segmentation approach localizes the seeds using a match filtering approach after the needle implants them in the brachytherapy procedure. Note that we have implemented a tri-bar line segment filter; however, other filters may be used. The method consists of five steps: needle segmentation, volume cropping, tri-bar model analysis, seed voxel classification and seed localization.

Needle segmentation: In the prostate brachytherapy procedure, usually up to 5 seeds per needle are implanted into the prostate. Thus, the positions of seeds will be constrained in a cuboid or cylindrical region along the needle trajectory. From the 3D TRUS image containing a needle, i.e., the image before withdrawing the needle, the position and orientation of the needle can be determined in near real-time by using needle segmentation or tracking techniques.

Volume cropping: After the needle determination in the needle segmentation, the 3D TRUS image volume is cropped as a cuboid i.e., $[x_{min}, x_{max}] \times [y_{min}, y_{max}] \times [z_{min}, z_{max}]$, where $x_{min} = \min(x_1 - \Delta x, x_1 - \Delta x + L(\cos\alpha - \psi)), x_{max} = \min(x_1 + \Delta x, x_1 + \Delta x + L(\cos\alpha + \psi))$, $y_{min} = \min(y_1 - \Delta y, y_1 - \Delta y + L(\cos\beta - \psi)), y_{max} = \min(y_1 + \Delta y, y_1 + \Delta y + L(\cos\beta + \psi))$, $z_{min} = \min(z_1 - \Delta z, z_1 - \Delta z + L(\cos\gamma - \psi)), z_{max} = \min(z_1 + \Delta z, z_1 + \Delta z + L(\cos\gamma + \psi))$.

$(x_1, y_1, z_1)$ is the 3D coordinates of the insertion point of the needle, L is the length of the needle, $(\cos\alpha, \cos\beta, \cos\gamma)$ is the needle direction vector, $\psi$ is the largest angle between the needle direction and the line of any pair of the seeds implanted by the same needle.

Tri-bar model analysis: based non-seed structure removal. We assume that the needle delivering the seeds is inserted approximately along the transducer axis of the ultrasound imaging system, i.e., the Z-axis of the 3D coordinate system. Thus, the ultrasound image of the seed shows strong parallel reflections from two layers related to the seeds: one between tissue and the lower surface of the seed, and the other from the interface between the upper surface of the seed and tissue. Suppose we intersect the 3D image three times, each with a $W \times W \times L_0$ bar kernel located in the X-, Y- and Z-axis as shown in FIG. 2(b) (here W is the diameter of the seed, $L_0$ is the length of seed), and project the kernel along the X-, Y- and Z-axis respectively, we will find the following:

In the Z-axis projected kernel, two bright spots will appear because the seed is projected along its axis.

In the X-axis projected kernel, two parallel line segments will appear because the seed is projected from the side direction of the seed (see FIG. 2(a)).

In the Y-axis projected kernel, a square structure will appear. Because when the seed is projected from the bottom, the upper and lower reflecting surfaces of the seed overlap, forming a uniform gray value area.

By calculating the standard deviation on each projected kernel, the following relationship has to be satisfied at a seed point $$\sigma_Z \geq k_1 \cdot \sigma_Y \geq k_2 \cdot \sigma_X \quad (1)$$

Where $\kappa_1, \kappa_2$ are two constants larger than 1.0. In our experiment, $k_1=2.0$ $k_2=4.0$. was used. One of the most important advantages of using the tri-bar model is that it can efficiently distinguish non-seed structures from seeds. Furthermore, the parameters noted used above do not directly depend on the voxel gray value of the seed in the 3D TRUS image, making our method more robust to variation of the voxel gray values in the image or of the seeds, either from different patients or using different settings of the imaging system.

Seed voxel classification: After application of the tri-bar model algorithm in the tri-bar model analysis, most of the non-seed structures are eliminated, but not all. In order to reduce high gray value structures further, especially the structures produced by intra-prostatic calcifications and avoid the detection of the square surface of the seed reflection, a 3D frame difference image, $d(i,j,k)$ was calculated, using the definition of $d(i,j,k)=f(i,j,k)-f(i,j,k-1)$, where $f(i,j,k), f(i,j,k-1)$, are two adjacent scanning slices of the 3D TRUS image. Now, two reflecting square surfaces of each seed in the 3D US image will produce four line segments in its 3D frame difference image. Using the following steps, we can recognize seed voxels.

3D line segment pattern calculation. Brachytherapy seeds are cylindrical, approximate 4.5 mm long with 0.8 mm diameter. By analyzing sample ultrasound images of seeds, we can determine the volume of the seed in the ultrasound image represented by a cuboid of $W \times W \times L_0$. In our experiment, we used $W=1.0$ mm, $L_0=5.0$ mm. At each point on the top surface of the Z-axis bar (see FIG. 2(b)), $(i, j, L_0/2)$, $-W/2 \leq i, j \leq W/2$, a straight line connecting $(i,j,L_0/2)$ and the center of the bar is determined. In the bar, all closest points to the line will form a 3D segment, i.e., the dark line in FIG. 2(b). All these line segments are called 3D line segment patterns.

The voxel gray values along each line segment pattern are added separately and the maximum sum, $sum_{max}$ of the gray levels is calculated. A 3D line segment is detected if $$sum_{max} > m_0, std < d_0, \quad (2)$$

where $sum_{max}$ are the maximum sum of voxel intensities in all line segment patterns, while std is the gray value standard deviation over the points on the maximum gray value line segment.

Seed localization: After Steps 3 & 4 are completed, all seed voxels are found in the 3D US image. We used the peak detection algorithm described in Ref. [18] to localize the center of the seed. The procedure is described as follows:

Maximum line segment calculation: For a point (i,j,k), if it satisfies Eqs. (1) and (2), we recognize it as a seed voxel and let $m(i,j,k)=\text{sum}_{max}$.

Average sum intensity calculation: Because each seed contains at least four line segments in the frame difference image, therefore, for a point, (i,j,k), we measure its probability belonging to a seed by averaging the maximum gray values of line segment patterns over the area of the seed, i.e., $$a(i,j,k) = \sum_{i_0=-W/2}^{W/2} \sum_{j_0=-L_0/2}^{L_0} \sum_{k_0=-W/2}^{W/2} m(i+i_0, j+j_0, k+k_0). \quad (3)$$

Seed center determination: Suppose (i,j,k), is a point with the maximum average value and satisfies the following two conditions:

$$a(i,j,k)=\max\{m(i',j',k'),(i',j'k')\in N_{25}\}. \quad (4)$$

$$a(i,j,k)=\max\{m(i',j',k'),(i',j'k')\in N_{98}\}. \quad (5)$$

Where $N_{26}$, $N_{98}$ represent the 26 and 98 surface voxels of 3×3×3 and 5×5×5 neighbors centered at (i,j,k), the point (i,j,k), is considered as the center of seed; otherwise it is a seed voxel instead of the center of the seed.

These steps are repeated until all seeds have been dropped and localized.

A second alternative method of using a priori information based on needle trajectory information. The algorithm will use 4 steps: volume cropping, adaptive thresholding, seed candidate extraction, and seed identification.

Volume cropping: By using the real-time needle-tracking algorithm as described above are able to follow the needle tip. Using this knowledge, the approximate cylindrical volume into which a seed has been deposited can be determined. Thus, the real-time 2D US image is continuously cropped to a small region where the seed should be located. The region of interest will start with a 3 mm diameter cylinder. This greatly eases the segmentation task and reduces computational time.

Adaptive thresholding: The cropped volume is segmented using an adaptive thresholding technique using histogram analysis. The threshold value must be small enough so that pixels above the threshold include as many of the seeds as possible (for high true positive rate), but large enough to exclude as many false candidates as possible (for low false positive rate). This operation results in a binary image with seed candidates pixels assigned a value of 1, and the remaining a value of 0.

Seed candidate extraction: Morphological image processing are used to remove isolated pixels and join small clusters. Each remaining connected group of pixels will be considered to be a seed candidate and labeled for analysis.

Seed identification: Features for each seed cluster are then determined, i.e., size, mean gray level, direction of its principal axis, and the angle between the principal axis and the segmented needle trajectory. Based on criteria of duster direction and size, clusters that appear to be of the same seed are joined. Finally, the seed using the clusters' features are localized and features determined from a set of manually segmented seeds.

3D seed segmentation: Using the recorded deposited seed locations, the seed search in the 3D TRUS image for the post-plan can be initialized. Although, the prostate will swell during the implantation, the deposition information and displacements of seeds can be identified to help in the search for the more difficult seeds to segment.

Other alternative methods for needle segmentation for purposes of facilitating seed segmentation will occur to those skilled in the art.

While the method of seed segmentation in a target volume in an ultrasound imaging system and the method of imaging using an ultrasound imaging system have been described with specificity to a rotational US scanning method, other types of scanning methods will occur to those of skill in the art. For example, the same approach can be used with a linear US scanning method. In addition, the segmentation method can be applied equally well to 3D US images reconstructed using the linear scanning geometry, but acquired using rotational 3D scanning geometry such as that used in prostate imaging.

The linear regression analysis approach for determining the needle trajectory from the difference map was selected as it requires relatively low processing power. A person of skill in the art, however, will appreciate that any method of determining the needle trajectory given the difference map can be used. For example, the well-known Hough Transform technique can be employed. The Hough Transform technique requires higher computational power than the linear regression approach, but this can be ignored where such processing power is available.

While a specific method of determining the GLC threshold was disclosed, other methods of determining the GLC threshold will occur to those skilled in the art. For example, a histogram of the greyscale-level values in the 3D US image can be generated and then analyzed to determine the regions of the histogram that most likely correspond to the background and to the needle. The analysis can be based on the statistical distribution of the greyscale-level values due to the acoustic scattering of the tissue and the statistical distribution of the specular reflection of the needle.

In addition to 3D applications, difference maps can be used to register movement in a single 2D plane. In this case, the difference map could represent a 2D plane and register differences between two 2D images.

While, in the above-described embodiment, the total length of the needle was used to determine the region of interest thereby to modify the scanning behavior of the TRUS transducer 24, one or more previous images could be used to estimate the expected seed implantation position. For example, where only the immediately previous image is available, the region of interest could include the current needle length in the image plus a relatively large distance along its trajectory beyond the needle tip. Where two previous images are available, the region of interest could include the current needle length plus a distance along its trajectory beyond the needle tip, wherein the distance is determined from movement of the needle registered from the two previous images.

It can be advantageous in some cases to compare a US image to one or more previous US images. For example, where the target volume is expected to shift, the initial image of the target volume prior to insertion of the needle may provide an inaccurate baseline image. By using more recent previous images, the target volume can be, in some cases, more readily filtered out to generate a cleaner difference map.

Where the robot is responsible for insertion of the needle and is controlled by an operator, feedback can be provided to the operator to simulate feedback that would generally be received were the operator performing the procedure directly. For example, where the operator is using a virtual needle to control the insertion of the needle by the robot, force feedback could be provided via the virtual needle to provide an indication of resistance encountered by the actual needle. Other forms of feedback could be visual, audio, etc.

The positioning of the needle trajectories can be continuous to provide a larger number of dosimetry possibilities.

Also, while the described approach has been described in conjunction with 3D TRUS imaging, equally the approach may be modified for use with other suitable real-time imaging techniques, including but not limited to certain magnetic resonance imaging or x-ray computed tomography imaging techniques.

The above-described embodiments are intended to be examples of the present invention and alterations and modifications may be effected thereto, by those of skill in the art, without departing from the scope of the invention which is defined solely by the claims appended hereto.

What is claimed is:

1. An apparatus for performing brachytherapy, comprising:
    a robotic assembly having a needle guide for guiding a brachytherapy needle during its insertion into a target volume of a patient, said robotic assembly being controllable to control the position and orientation of said needle guide in relation to said patient, said needle guide permitting manual longitudinal movement of said brachytherapy needle by an operator;
    a computing device in communication with said robotic assembly, said computing device storing a dose distribution for the target volume, said dose distribution comprising a set of planned needle trajectories, at least one of said planned needle trajectories being oblique with respect to other planned needle trajectories and a planned distribution of seeds along each of said planned needle trajectories, said computing device controlling said robotic assembly to position said needle guide in accordance with the set of planned needle trajectories of said dose distribution; and
    a three-dimensional ultrasound transducer for capturing volume data of said target volume, said computing device being in communication with and receiving said volume data from said ultrasound transducer, said computing device processing said volume data to determine an actual distribution of said seeds along actual needle trajectories, and dynamically adjusting the dose distribution to target cold spots and/or to compensate for deviations between actual needle trajectories and planned needle trajectories and/or shifting of the target volume.

2. The apparatus of claim 1, wherein said robotic assembly is controllable to provide variably adjustable positioning and orientation of said needle guide.

3. The apparatus of claim 1 wherein said robotic assembly comprises a robotic arm having five degrees of freedom, said robotic arm carrying said needle guide.

4. The apparatus of claim 1 wherein said robotic assembly is controllable to translate the needle guide in three dimensions and to rotate the needle guide about two orthogonal axes.

5. The apparatus of claim 3 wherein said needle guide is a single-holed template.

6. The apparatus of claim 3 wherein said computing device is configured to direct movement of the robotic arm in terms of a coordinate system fixed to the robotic arm.

7. The apparatus of claim 3 wherein said computing device is configured to direct movement of the robotic arm in terms of a coordinate system fixed to the ground.

8. An apparatus for performing brachytherapy, comprising:
    a robotic assembly having a needle guide for guiding a brachytherapy needle during its insertion into a target volume of a patient, said robotic assembly being configured to control the position and orientation of said needle guide in relation to said patient, said needle guide being configured to permit manual longitudinal movement of said brachytherapy needle by an operator;
    a computing device in communication with said robotic assembly, said computing device storing a dose distribution for the target volume, said dose distribution comprising a set of planned needle trajectories, at least one of said planned needle trajectories being oblique with respect to other planned needle trajectories and seed implantation locations along said planned needle trajectories, said computing device instructing said robotic assembly to position said needle guide allowing insertion of the needle into the target volume of the patient along the planned needle trajectories; and
    a three-dimensional ultrasound transducer configured to capture volume data of said target volume, said computing device being in communication with and receiving said volume data from said ultrasound transducer, said computing device processing said volume data using dose planning software to re-determine dosimetry based on actual needle trajectories and seed implantation locations.

9. The apparatus of claim 8, wherein said robotic assembly is configured to variably adjust positioning and orientation of said needle guide.

10. The apparatus of claim 8 wherein said robotic assembly comprises a robotic arm having five degrees of freedom, said robotic arm carrying said needle guide.

11. The apparatus of claim 8 wherein said robotic assembly is configured to translate the needle guide in three dimensions and to rotate the needle guide about two orthogonal axes.

12. The apparatus of claim 10 wherein said needle guide is a single-holed template.

13. The apparatus of claim 10 wherein said computing device is configured to direct movement of the robotic arm in terms of a coordinate system fixed to the robotic arm.

14. The apparatus of claim 10 wherein said computing device is configured to direct movement of the robotic arm in terms of a coordinate system fixed to the ground.

* * * * *